United States Patent
Castor et al.

(10) Patent No.: US 7,032,592 B2
(45) Date of Patent: Apr. 25, 2006

(54) GAS DOSING DEVICE

(75) Inventors: Rolf Castor, Hägersten (SE); Pär Emtell, Vällingby (SE)

(73) Assignee: Maquet Critical Care AB, Solna (SE)

( * ) Notice: Subject to any disclaimer, the term of this patent is extended or adjusted under 35 U.S.C. 154(b) by 23 days.

(21) Appl. No.: 10/457,606

(22) Filed: Jun. 9, 2003

(65) Prior Publication Data

US 2003/0230306 A1 Dec. 18, 2003

(30) Foreign Application Priority Data

Jun. 18, 2002 (SE) .............................................. 0201855

(51) Int. Cl.
*A62B 18/08* (2006.01)

(52) U.S. Cl. .............................. 128/201.13; 128/205.27; 128/205.28; 128/206.17; 128/204.11

(58) Field of Classification Search ............ 128/201.13, 128/205.27, 205.25, 206.17, 204.11; 165/119; 55/486, 487; 392/396
See application file for complete search history.

(56) References Cited

U.S. PATENT DOCUMENTS

| 4,048,993 | A | * | 9/1977 | Dobritz ................. 128/201.13 |
| 4,327,717 | A | | 5/1982 | Oetjen et al. |
| 4,708,831 | A | * | 11/1987 | Elsworth et al. ............. 261/130 |
| 5,031,612 | A | * | 7/1991 | Clementi ................ 128/204.14 |
| 5,845,633 | A | * | 12/1998 | Psaros .................... 128/200.24 |
| 5,906,201 | A | | 5/1999 | Nilson |
| 6,102,042 | A | * | 8/2000 | Hete et al. ............. 128/207.16 |
| 6,116,235 | A | * | 9/2000 | Walters et al. ......... 128/200.24 |
| 6,397,842 | B1 | * | 6/2002 | Lee ........................ 128/203.26 |
| 2002/0002976 | A1 | * | 1/2002 | Smith et al. |

FOREIGN PATENT DOCUMENTS

| EP | 1 153 627 | 11/2001 |
| WO | WO 82/03014 | 8/1982 |
| WO | WO 01/19526 | 12/1991 |
| WO | WO 01/72365 | 10/2001 |

* cited by examiner

*Primary Examiner*—Glenn K. Dawson
*Assistant Examiner*—Michael Mendoza
(74) *Attorney, Agent, or Firm*—Schiff Hardin LLP

(57) ABSTRACT

A device for the dosing of a dry additive gas into a breathing gas in a ventilator system, the ventilator system including a tubing system connectable by at a distal end to a patient, and has a dosing tube connectable to the tubing system for dosing to the distal end of the tubing system. The dosing tube is composed of a tube section having a moisture permeable contact surface, adapted to interact with moisture from exhaled breathing gas, so the dry additive gas is humidified before dosing to the distal end of the tubing system.

4 Claims, 1 Drawing Sheet

GAS DOSING DEVICE

BACKGROUND OF THE INVENTION

1. Field of the Invention

The present invention relates to a device for dosing a gas, particularly in a ventilator system.

2. Description of the Prior Art

Supply of an additive gas by means of a dosing tube is described, for example, in PCT Application WO 91/19526. The intention is, in this case, to reduce the re-breathing of carbon dioxide. Fresh dry gas can be transported down to the trachea in order to flush away exhaled gas which comes from the lungs and which would normally be re-breathed with the next breath (dead space).

The supply of dry gas can result in dehydration of a patient. This is especially the case if large quantities of dry gas are supplied in this manner. This is not desirable and can result in injury to the patient.

Another purpose for the delivery of an additive gas can be to provide therapy in the form of high frequency pulses superimposed on normal ventilation, such as is described in PCT Application WO 82/03014. In this case the additive high frequency gas may be humidified before it is introduced into the tubing system of the medical ventilator. This is done mainly because larger gas amounts are involved than normally occur in the applications according to WO 91/19526.

Active humidification of an additive gas, however, means additional costs because the humidifier must be monitored, etc. Risk to the patient increases in the event of the active humidifier ceasing to function.

There is thus a need for a simple, inexpensive and effective solution to these problems.

SUMMARY OF THE INVENTION

An object of the present invention is to provide a device for dosing a dry additive gas that at least alleviates some of the problems associated with the current state of the art.

This object is achieved in accordance with the invention in a dosing device for dosage of a dry additive gas into a breathing gas in a ventilator system, wherein the ventilator system includes a tubing system connectable at a distal end to a patient, and wherein the dosing device includes a dosing tube connectable to the tubing system for dosing the additive gas at the distal end of the tubing system, and wherein the dosing tube includes a tube section having a moisture permeable contact surface which interacts with moisture from exhaled breathing gas so that the dry additive gas is humidified before dosing thereof at the distal end of the tubing system.

With a part of (or the whole) dosing tube formed of moisture permeable material, moisture from the expired gas can be taken up in the dry additive gas.

A moisture and heat exchanger can be formed so that a moisture permeable tube runs within it in order to humidify an additive gas supplied via the tube simultaneously with the transfer by the moisture and heat exchanger of moisture and heat from exhaled gas to fresh breathing gas during the successive inhalation.

The dry additive gas may be taken from a separate gas source or from the same source used by the ventilator (when the additive gas is identical to one of the gases in the breathing gas, for example oxygen). In the latter case the additive gas may be taken from the ventilator.

DESCRIPTION OF THE PREFERRED EMBODIMENTS

Figure 1:
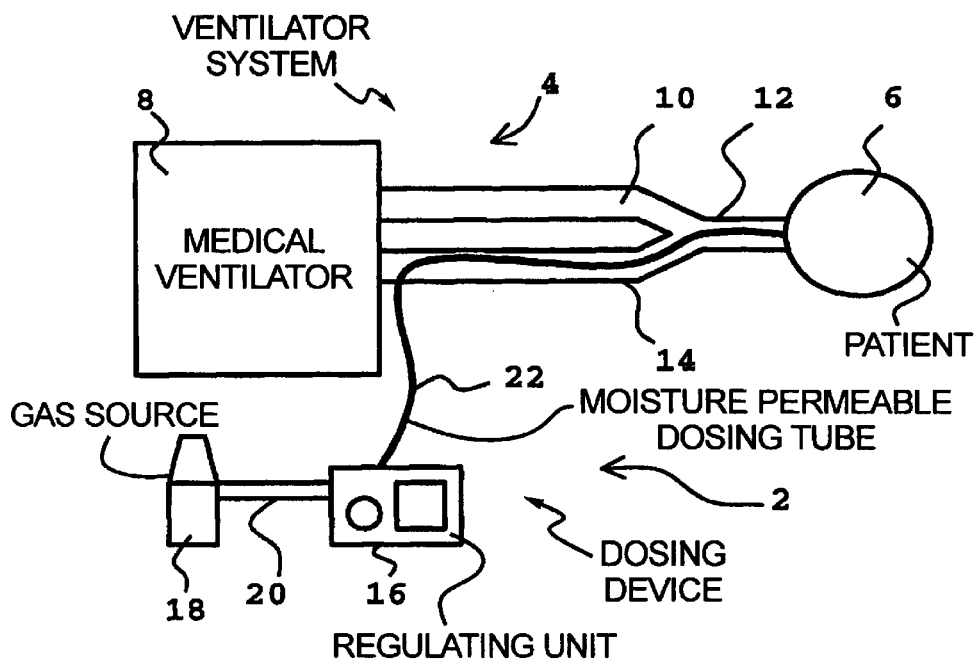
FIG. 1 shows a first embodiment of a device according to the invention.

A device 2 for dosing an additive gas is shown in FIG. 1 as a first exemplary embodiment of the invention. The device 2 is connected to a ventilator system 4 that supplies a patient 6 with a breathing gas. The ventilator system 4 basically includes a medical ventilator 8 and a tubing system containing an inspiration tube 10, a patient tube 12 and an expiration tube 14. Breathing gas is supplied to the patient 6 via the inspiration tube 10 and the patient tube 12 and is led away from the patient 6 via the expiration tube 14 and the patient tube 12.

The device 2 includes a regulating unit 16 for the regulation of pressure/flow, quantity, etc. during the dosing. The regulating unit 16 may also have a user interface (indicated in FIG. 1). In the present case the regulating unit 16 receives the dry additive gas from a separate gas source 18 connected to the regulating unit 16 by means of a feed tube 20.

The dosed gas is led through a dosing tube 22 to the distal part of the tubing system 10, 12, 14, more precisely, to the lower part of the patient tube 12 for dosing the additive gas to the patient 6.

In accordance with the state of the art the gas, in this case, may be supplied during the end phase of expiration in order to reduce re-breathing from the dead space. It may also be used for the dosing of nitrous oxide gas at the beginning of inspiration or for other applications.

In the present embodiment of the device 2 the entire dosing tube 22 is basically composed of a moisture permeable material, preferably NAFION®. Moisture is taken up from the surroundings along the entire dosing tube 22. Moreover in this case the main part of the dosing tube 22 runs within the expiration tube 14. The exhaled gas with its high moisture content will quickly raise the moisture level in the additive gas. There is thus no risk of dehydration of the patient 6 as a consequence of the additive gas.

Figure 2:
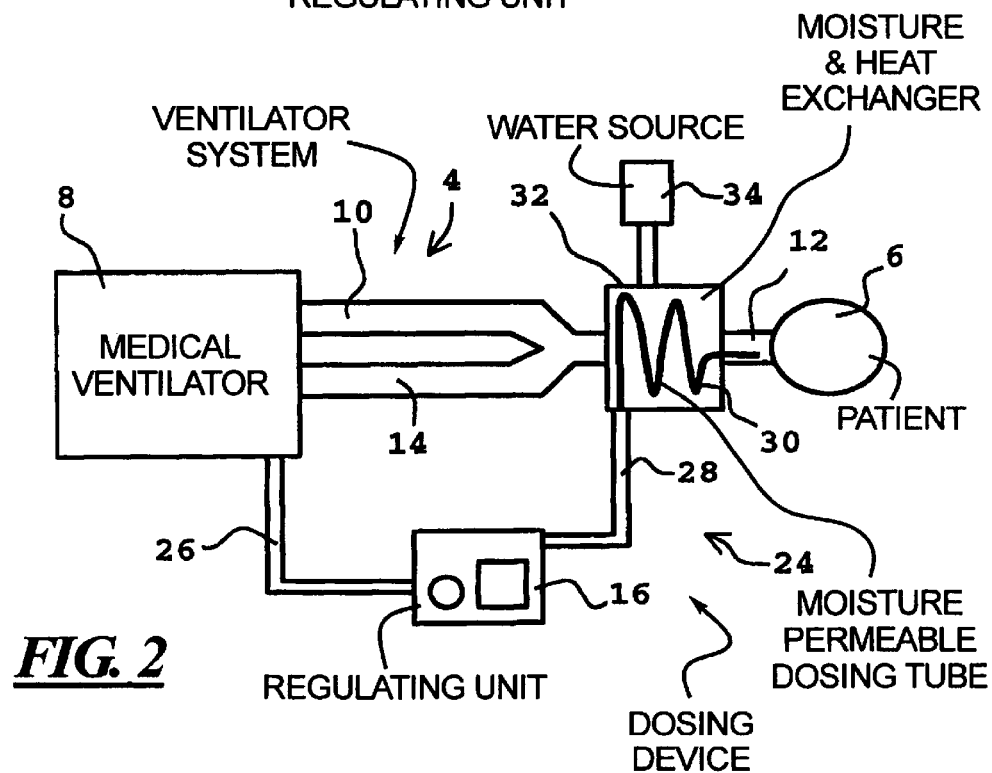
FIG. 2 shows a second embodiment of a device according to the invention.

A second exemplary embodiment will be described with reference to FIG. 2. Components that can be identical to the previous embodiment have been accorded the same reference numerals.

A device 24 for dosing an additive gas is connected to a ventilator system 4 for the supply of breathing gas to a patient 6. The ventilator system 4 includes a medical ventilator 8 and a tubing system having an inspiration tube 10, a patient tube 12 and an expiration tube 14. Breathing gas is supplied to the patient 6 via the inspiration tube 10 and the patient tube 12 and is led away from the patient 6 via the expiration tube 14 and the patient tube 12.

In their exemplary embodiment, as in the previous exemplary embodiment, the device 24 has a regulating unit 16. A feed tube 26 is connected to the medical ventilator 8 that acts as a source of additive gas for the device 24.

The additive gas is led from the regulating unit 16 via a dosing tube 28 to the distal part of the patient tube 12 for dosing. The dosing tube 28 has, as a part of it, a tube section 30 formed of a moisture permeable material. The tube section 30 is arranged in a moisture and heat exchanger 32.

The moisture and heat exchanger 32 takes up moisture and heat from exhaled gas and transfers it to the inhaled gas.

As the tube section 30 is arranged in the moisture and heat exchanger 32 moisture will be uniformly transferred to the dry additive gas within the tube section 30.

A water source 34 may be connected to the moisture and heat exchanger 32 in order to compensate for moisture losses (the moisture and heat exchanger 32 does not have a 100% take up and re-supply of moisture).

The two exemplary embodiments can be combined in suitable ways. For example a smaller tube section with moisture permeable qualities can be provided in the first exemplary embodiment and an entire dosing tube formed of moisture permeable material in the second exemplary embodiment. The gas sources of the respective embodiments also can be interchanged.

Although modifications and changes may be suggested by those skilled in the art, it is the intention of the inventors to embody within the patent warranted hereon all changes and modifications as reasonably and properly come within the scope of their contribution to the art.

We claim as our invention:

1. In a ventilator system having a tubing system adapted for connection at a distal end to a patient, said tubing system including a respiratory part having an expiratory part, the improvement of a dosing device for adding a dry additive gas into breathing gas in said tubing system, comprising:

a dosing tube connectable to said tubing system and having a first end adapted for connection to a source of dry additive gas and a second end for dosing said dry additive gas into said breathing gas at said distal end of said tubing system; and said dosing tube comprising a tube section between said first and second ends and disposed in said expiratory part, said tube section having a moisture permeable contact surface adapted for interaction with moisture from exhaled breathing gas in said expiratory part and for interacting with said dry additive gas for humidifying said dry additive gas before dosing of said additive gas at said distal end of said tubing system.

2. The improvement of claim 1 wherein said device comprises a moisture exchanger in which said tube section is disposed, said moisture exchanger being adapted for coupling into said tubing system.

3. The improvement of claim 1 wherein said device further comprises a feed tube adapted for connection to a source of said dry additive gas.

4. The improvement of claim 3 wherein said gas source is disposed within said ventilator system.

* * * * *